US008658659B2

(12) United States Patent
Grierson et al.

(10) Patent No.: US 8,658,659 B2
(45) Date of Patent: Feb. 25, 2014

(54) SUBSTITUTED OXAZOLE DERIVATIVES AND THEIR USE AS TYROSINE KINASE INHIBITORS

(75) Inventors: David Grierson, Versailles (FR); Abdellah Benjahad, Champigny sur Marne (FR); Alain Moussy, Paris (FR); Martine Croisy, Cernay la Ville (FR)

(73) Assignees: AB Science, Paris (FR); Centre National de la Recherche Scientifique (CNRS), Paris (FR); Institut Curie, Paris (FR)

( * ) Notice: Subject to any disclaimer, the term of this patent is extended or adjusted under 35 U.S.C. 154(b) by 0 days.

(21) Appl. No.: 13/343,968

(22) Filed: Jan. 5, 2012

(65) Prior Publication Data
US 2012/0108616 A1 May 3, 2012

Related U.S. Application Data

(63) Continuation of application No. 11/910,497, filed as application No. PCT/IB2006/001249 on Apr. 4, 2006, now abandoned.

(60) Provisional application No. 60/667,771, filed on Apr. 4, 2005.

(51) Int. Cl.
| C07D 263/46 | (2006.01) |
| C07D 263/58 | (2006.01) |
| C07D 413/04 | (2006.01) |
| C07D 413/12 | (2006.01) |
| C07D 413/14 | (2006.01) |
| C07D 417/12 | (2006.01) |

(52) U.S. Cl.
USPC .......... 514/274; 514/340; 514/341; 514/377; 544/316; 546/271.4; 548/234

(58) Field of Classification Search
None
See application file for complete search history.

(56) References Cited

U.S. PATENT DOCUMENTS

| 3,740,420 A | 6/1973 | Herschler et al. |
| 3,743,727 A | 7/1973 | Herschler |
| 3,772,295 A | 11/1973 | Robba et al. |
| 3,989,816 A | 11/1976 | Rajadhyaksha |
| 4,322,433 A | 3/1982 | Leslie et al. |
| 4,343,940 A | 8/1982 | Kreighbaum et al. |
| 4,379,454 A | 4/1983 | Campbell et al. |
| 4,405,616 A | 9/1983 | Rajadhyaksha |
| 4,411,893 A | 10/1983 | Johnson et al. |
| 4,460,372 A | 7/1984 | Campbell et al. |
| 4,575,515 A | 3/1986 | Sandborn |
| 4,615,699 A | 10/1986 | Gale et al. |
| 5,217,999 A | 6/1993 | Levitzki et al. |
| 5,302,606 A | 4/1994 | Spada et al. |
| 5,330,992 A | 7/1994 | Eissenstat et al. |
| 5,521,184 A | 5/1996 | Zimmermann |
| 5,556,611 A | 9/1996 | Biesalski |
| 5,656,643 A | 8/1997 | Spada et al. |
| 5,710,158 A | 1/1998 | Myers et al. |
| 5,714,493 A | 2/1998 | Myers et al. |
| 5,721,237 A | 2/1998 | Myers et al. |
| 5,792,783 A | 8/1998 | Tang et al. |
| 5,834,504 A | 11/1998 | Tang et al. |
| 5,883,116 A | 3/1999 | Tang et al. |
| 5,886,020 A | 3/1999 | Tang et al. |
| 5,906,202 A | 5/1999 | Schuster et al. |
| 6,331,553 B1 | 12/2001 | Esaki et al. |
| 7,718,676 B2 | 5/2010 | Moussy et al. |

FOREIGN PATENT DOCUMENTS

| EP | 0 602 851 B1 | 10/1996 |
| EP | 0 520 722 B1 | 12/1996 |
| EP | 0 584 222 B1 | 10/1997 |
| EP | 0 934 931 A2 | 8/1999 |
| RU | 2193554 | 12/1997 |
| WO | WO 91/15495 A1 | 10/1991 |
| WO | WO 92/20642 A1 | 11/1992 |
| WO | WO 92/21660 A1 | 12/1992 |
| WO | WO 94/03427 A1 | 2/1994 |
| WO | WO 94/14808 A1 | 7/1994 |
| WO | WO 95/15758 A1 | 6/1995 |
| WO | WO 96/40116 A1 | 12/1996 |
| WO | WO 99/03854 A1 | 1/1999 |
| WO | WO 00/38519 A1 | 7/2000 |
| WO | WO 03/002105 A2 | 1/2003 |
| WO | WO 03/002106 A2 | 1/2003 |
| WO | WO 03/002107 A2 | 1/2003 |
| WO | WO 03/002108 A2 | 1/2003 |
| WO | WO 03/002109 A2 | 1/2003 |
| WO | WO 03/002114 A2 | 1/2003 |
| WO | WO 03/003004 A2 | 1/2003 |
| WO | WO 03/003006 A2 | 1/2003 |
| WO | WO 03/004006 A2 | 1/2003 |

(Continued)

OTHER PUBLICATIONS

Dugard et al., "Effects of Ionic Surfactants on the Permeability of Human Epidermis: An Electrometric Study," *The Journal of Investigative Dermatology*, vol. 60, No. 5, pp. 263-269, 1973.
Nairn, "Solutions, Emulsions, Suspensions and Extractives," *Remington's Pharmaceutical Sciences*, $16^{th}$ ed., pp. 1438-1462, 1980.
Beghini et al., "C-kit mutations in core binding factor leukemias," *Blood*, vol. 95, No. 2, pp. 726-727, Jan. 15, 2000.
Longley et al., "Classes of c-*KIT* activating mutations: proposed mechanisms of action and implications for disease classification and therapy," *Leukemia Research*, vol. 25, pp. 571-576, 2001.
Longley et al., "Somatic c-KIT activating mutation in urticaria pigmentosa and aggressive mastocytosis: establishment of clonality in a human mast cell neoplasm," *Nature Genetics*, vol. 12, pp. 312-314, Mar. 12, 1996.

(Continued)

Primary Examiner — Kamal Saeed
(74) Attorney, Agent, or Firm — Foley & Lardner LLP

(57) ABSTRACT

The present invention relates to novel compounds selected from substituted oxazole derivatives of formula (I) that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit, bcr-abl and Flt-3 inhibitors.

13 Claims, No Drawings

(56) References Cited

FOREIGN PATENT DOCUMENTS

| WO | WO 03/004007 A2 | 1/2003 |
| WO | WO 03/035049 A2 | 5/2003 |
| WO | WO 03/035050 A2 | 5/2003 |
| WO | WO 03/039550 A1 | 5/2003 |
| WO | WO 03/062215 A1 | 7/2003 |
| WO | WO 2004/001059 A2 | 12/2003 |
| WO | WO 2004/032882 A1 | 4/2004 |
| WO | WO 2005/000298 A2 | 1/2005 |
| WO | WO 2005/040139 | 5/2005 |

OTHER PUBLICATIONS

Kim et al., "Inhibition of vascular endothelial growth factor-induced angiogenesis suppresses tumour growth in vivo," Nature, vol. 362, pp. 841-844, Apr. 29, 1993.

Broudy, "Stem Cell Factor and Hematopoiesis," Blood, vol. 90, No. 4, pp. 1345-1364, 1997.

Cooper et al., "Interaction of Surfactants with Epidermal Tissues: Physicochemical Aspects," Surfactant Science, Reiger, M.M. ed., Marcel Dekker, Inc., pp. 195-210, 1987.

Sekura et al., "The Percutaneous Absorption of Alkyl Methyl Sulfoxides," Adv. Biol. Skin, Chapter 12, pp. 257-269, 1972.

Harris et al., "Discovery and Evaluation of 2-Amino-5-aryloxazoles as a novel clas of VEGFR2 kinase inhibitors," J. Med. Chem., vol. 48, pp. 1610-1619, 2005.

Office Action issued by the Examiner in U.S. Appl. No. 11/910,497 on Aug. 5, 2011.

Office Action issued by the Examiner in U.S. Appl. No. 11/910,497 on Feb. 18, 2011.

Office Action issued by the Examiner in U.S. Appl. No. 11/910,497 on Sep. 29, 2010.

Yu et al., "Mast cells can promote the development of multiple features of chronic asthma in mice," The Journal of Clinical Investigation, vol. 116, No. 6, pp. 1633-1641, Jun. 2006.

Brown et al., "Mechanisms underlying mast cell influence on EAE disease course," Molecular Immunology, vol. 38, pp. 1373-1378, 2001.

Benoist et al., "Mast cells in autoimmune disease," Nature, vol. 420, pp. 875-878, Dec. 2002.

Bradding et al., "The role of the mast cell in the pathophysiology of asthma," J. Allergy Clin. Immunol., vol. 117, No. 6, pp. 1277-1284, Jun. 2006.

Galinsky et al., "Mast cells and cancer—No longer just basic science," Critical Reviews in Oncology/Hematology, vol. 68, pp. 115-130, 2008.

Tristano, "Tyrosine kinases as targets in rheumatoid arthritis," International Immunopharmacology, vol. 9, pp. 1-9, 2009.

Zappulla et al., "Mast cells: new targets for multiple sclerosis therapy?," Journal of Neuroimmunology, vol. 131, pp. 5-20, 2002.

SUBSTITUTED OXAZOLE DERIVATIVES AND THEIR USE AS TYROSINE KINASE INHIBITORS

CROSS-REFERENCE TO RELATED APPLICATIONS

This application is a continuation of U.S. application Ser. No. 11/910,497, filed Oct. 2, 2007, which is a national stage of PCT/IB2006/001249, filed under 35 U.S.C. §371. PCT/IB2006/001249, filed Apr. 4, 2006, is published in the English language as International Publication No. WO 2006/106437 A3, and claims the benefit of U.S. Provisional Application No. 60/667,771, filed Apr. 4, 2005. Each of the above applications is incorporated herein by reference for all purposes.

The present invention is concerned with substituted oxazole derivatives that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit, bcr-abl and Flt-3 inhibitors.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Included are the well-known VEGF receptors (Kim et al., Nature 362, pp. 841-844, 1993), PDGF receptors, c-kit, Flt-3 and the FLK family. These receptors can transmit signals to other tyrosine kinases including Src, Raf, Frk, Btk, Csk, Abl, Fes/Fps, Fak, Jak, Ack, etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, U.S. 60/359,652, U.S. 60/359,651 and U.S. 60/449,861.

It was found that mast cells present in tissues of patients are implicated in or contribute to the genesis of diseases such as autoimmune diseases (rheumatoid arthritis, inflammatory bowel diseases (IBD)) allergic diseases, bone loss, cancers such as solid tumors, leukaemia and GIST, tumor angiogenesis, inflammatory diseases, interstitial cystitis, mastocytosis, graft-versus-host diseases, infection diseases, metabolic disorders, fibrosis, diabetes and CNS diseases. In these diseases, it has been shown that mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor also can be constitutively activated by mutations leading to abnormal cell proliferation and development of diseases such as mastocytosis (D816V mutation) and various cancers such as GIST (c-kitΔ27, a juxtamembrane deletion).

Sixty to 70% of patients presenting with AML have blasts which express c-kit, the receptor for stem cell factor (SCF) (Broudy, 1997). SCF promotes growth of hematopoietic progenitors, and act as a survival factor for AML blasts. In some cases (1 to 2%) of AML, a mutation in a conserved residue of the kinase domain (Kit816) resulting in constitutive activation of c-kit has been described (Beghin et al., 2000; Longley et al., 2001). This gain of function mutation (Asp to Val/Tyr substitution) has been identified in mast cell leukemic cell lines and in samples derived from patients with mastocytosis (Longley et al., 1996). Preliminary results show that this mutation is expressed in most cases of systemic mastocytosis ([~60%], P Dubreuil, AFIRMM, study in progress on about 300 patients).

For this reason, it has been proposed to target c-kit to deplete the mast cells responsible for these disorders.

The main objective underlying the present invention is therefore to find potent and selective compounds capable of inhibiting wild type and/or mutated c-kit.

Many different compounds have been described as tyrosine kinase inhibitors, for example, bis monocyclic, bicyclic or heterocyclic aryl compounds (WO 92/20642), vinylene-azaindole derivatives (WO 94/14808), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), selenoindoles and selenides (WO 94/03427), tricyclic polyhydroxylic compounds (WO 92/21660), benzylphosphonic acid compounds (WO 91/15495), pyrimidine derivatives (U.S. Pat. No. 5,521,184 and WO 99/03854), indolinone derivatives and pyrrole-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940) and aryl and heteroaryl quinazoline (U.S. Pat. No. 5,721,237, U.S. Pat. No. 5,714,493, U.S. Pat. No. 5,710,158 and WO 95/15758).

However, none of these compounds have been described as potent and selective inhibitors of c-kit or of the c-kit pathway.

In connection with the present invention, we have discovered that compounds displaying specific substitutions in oxazole derivatives are potent and selective inhibitors of c-kit, bcr-abl, Flt-3 or c-kit pathway. These compounds are good candidates for treating diseases such as autoimmunes diseases, inflammatory diseases, cancers and mastocytosis.

DESCRIPTION

Therefore, the present invention relates to compounds belonging to the substituted oxazole derivatives. These compounds are capable of selectively inhibiting signal transduction involving the tyrosine phosphokinase c-kit, bcr-abl, Flt-3 and mutant forms thereof.

In a first embodiment, the invention is aimed at compounds of formula I, which may represent either free base forms of the substances or pharmaceutically acceptable salts thereof:

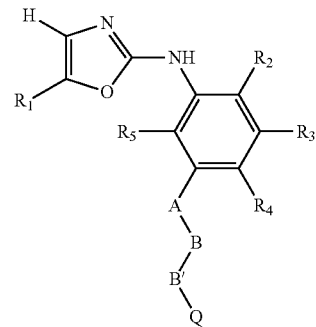

FORMULA I wherein substituents A, B, B', Q and R1-R5 in Formula I are defined as follows:

A and B' is one of the following:
i) (R6)N(CH$_2$)$_n$ where n is 0 or 1
ii) O(CH2)$_n$ where n is 0 or 1
iii) S(CH2)$_n$ where n is 0 or 1
iv) (CH2)$_n$ where n is 0, 1 or 2
v) C(O)(CH2)$_n$ where n is 0 or 1
or when A and B' each are a nitrogen, they may be taken together to form a bivalent radical of formula:

—(CH2)$_s$-X1-(CH2)$_t$—  (a)

where s and t each independently is 1 or 2 and X1 being O, S, NR10, N[C(=O)R10] or (CH2)$_n$ where n is 0 or 1, and wherein each hydrogen in said formula (a) may be substituted with halo or C$_{1-4}$alkyl.

B is one of the following:
i) (R6)N
ii) Oxygen
iii) S(O)$_n$ where n is 0, 1 or 2
iv) CH(R6)(R7)
v) C=δ, where δ is oxygen, sulfur, NH or N—CN
vi) C(R6)=C(R7)
vii) N=C(R6)

R6 and R7 each independently are hydrogen, C$_{1-4}$alkyl, C$_{2-6}$alkenyl, C$_{2-6}$alkynyl, C$_{3-7}$cycloalkyl, C$_{1-4}$haloalkyl, C$_{1-4}$alkoxy, C$_{1-4}$hydroxyalkyl, C$_{1-4}$alkylamino.

R1 is selected from:
i) hydrogen, halogen (selected from F, Cl, Br or I), or
ii) an alkyl$^1$ group defined as a linear, branched or cycloalkyl group containing from 1 to 10 carbon atoms and optionally substituted with one or more hetereoatoms such as halogen (selected from F, Cl, Br or I), oxygen, and nitrogen (the latter optionally in the form of a pendant basic nitrogen functionality); as well as trifluoromethyl, carboxyl, cyano, nitro, formyl; as well as CO—R, COO—R, CONH—R, SO2-R, and SO2NH—R wherein R is a linear or branched alkyl group containing 1 to 10 carbon atoms and optionally substituted with at least one heteroatom, notably a halogen (selected from F, Cl, Br or I), oxygen, and nitrogen, the latter optionally in the form of a pendant basic nitrogen functionality; as well as a cycloalkyl or aryl$^1$ or heteroaryl$^1$ group optionally substituted by a pendant basic nitrogen functionality, or
iii) an aryl$^1$ group defined as phenyl or a substituted variant thereof bearing any combination, at any one ring position, of one or more substituents such as
halogen (selected from I, F, Cl or Br);
an alkyl$^1$ group;
a cycloalkyl, aryl or heteroaryl group optionally substituted by a pendant basic nitrogen functionality;
trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality;
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^1$, aryl or heteroaryl, or
iv) a heteroaryl$^1$ group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, benzoxazole, benzothiazole, quinolinyl group, which may additionally bear any combination, at any one ring position, of one or more substituents such as
halogen (selected from F, Cl, Br or I);
an alkyl$^1$ group;
a cycloalkyl, aryl or heteroaryl group optionally substituted by a pendant basic nitrogen functionality,
trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality;
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^1$, or
v) an O-aryl$^1$, or NH-aryl$^1$, or O-heteroaryl$^1$ or NH-heteroaryl$^1$ group
vi) trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality, or
vi) NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^1$, aryl$^1$ or heteroaryl$^1$.

R2, R3, R4 and R5 each independently are selected from hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; as well as trifluoromethyl, C$_{1-6}$alkyloxy, amino, C$_{1-6}$alkylamino, di(C$_{1-6}$alkyl)amino, carboxyl, cyano, nitro, formyl, hydroxy, and CO—R, COO—R, CONH—R, SO2-R, and SO2NH—R wherein R corresponds to hydrogen, alkyl$^1$, aryl or heteroaryl.

and wherein Q is selected from:
i) Alkyl$^1$
ii) Aryl$^1$
iii) Heteroaryl$^1$
as defined above.

In one particular embodiment, group Q is a substituted alkyl, aryl or heteroaryl group bearing a pendant basic nitrogen functionality represented for example by the structures a to m shown below, wherein the wavy line and the arrow line correspond to the point of attachment to core structure of formula I.

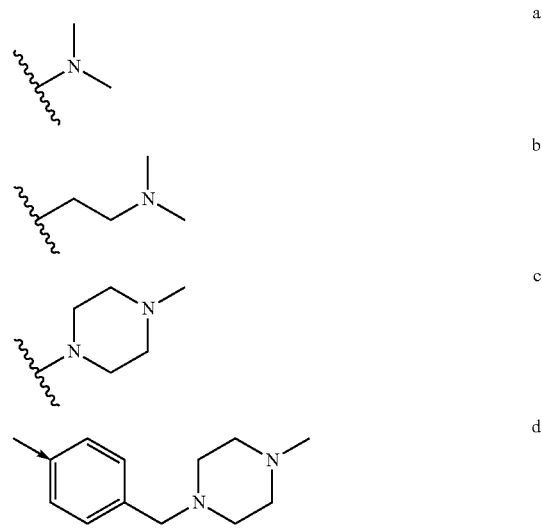

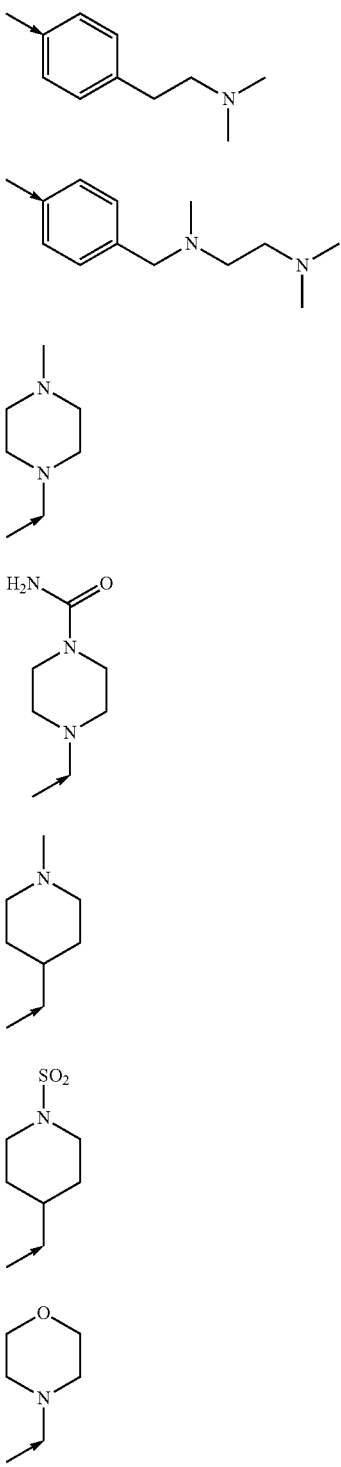

Also, for g to m, the arrow may include a point of attachment to the core structure via a phenyl group.

Furthermore, among the preferred compounds of formula I, II, III and IV, the invention concerns the compounds in which R1 is pyridyl or benzonitrile which may additionally bear any combination, at any one ring position, of one or more substituents such as hydrogen;

halogen (selected from F, Cl, Br or I);

an alkyl[1] group;

an aryl[1] group;

trifluoromethyl, O-alkyl[1], carboxyl, cyano, nitro, formyl, hydroxy, NH-alkyl[1], N(alkyl[1])(alkyl[1]), and amino, the latter nitrogen substituents optionally in the form of a basic nitrogen functionality;

NHCO—R or NHCOO—R or NHCONH—R or NHSO2-R or NHSO2NH—R or CO—R or COO—R or CONH—R or SO2-R or SO2NH—R wherein R corresponds to hydrogen, alkyl[1] or aryl[1] group.

Unless stated otherwise, for the purpose of the present invention, the term "alkyl group" is intended to mean any linear or branched, substituted or unsubstituted, C1-C10 alkyl group, such as C1-C4 or C1-C6, in particular a methyl, ethyl group, propyl group, preferably methyl. The term "alkenyl" as used in the present invention refers to C1-C6, in particular C1-C4, straight or branched chain substituted or unsubstituted alkenyl radicals containing from 1 to 30 carbon atoms including, but not limited to, ethenyl, propenyl, butenyl, pentenyl, hexenyl and the like. The term "alkoxy group" is intended to mean any alkoxy group having 1 to 6 linear or branched, substituted or unsubstituted, carbon atoms, in particular the group OCH3. The term "aryl group" is intended to mean one or more aromatic rings having 5 to 6 carbon atoms, which may be joined or fused, and substituted or unsubstituted. In particular, the aryl groups may be phenyl or pyridyl and the substituents may be halogen atoms, cyano, amino, alkoxy groups as defined above, alkyl groups as defined above or a nitro group.

An example of preferred compounds of the above formula is depicted below:

001: N-[4-Methyl-3-(5-pyridin-4-yl-oxazol-2-ylamino)-phenyl]-C-phenyl-methane sulfonamide

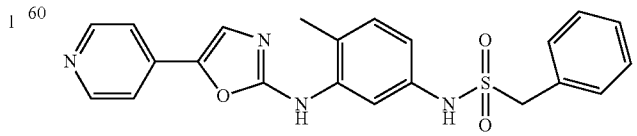

m.p.=258° C.

002: 4-{2-[5-(Benzooxazol-2-ylamino)-2-methyl-phenylamino]-oxazol-5-yl}-benzonitrile

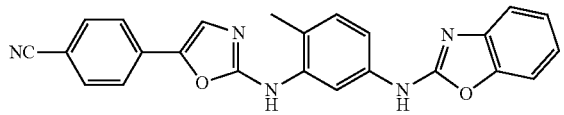

m.p.=236° C.

003: 4-{2-[5-(Benzothiazol-2-ylamino)-2-methyl-phenylamino]-oxazol-5-yl}-benzonitrile

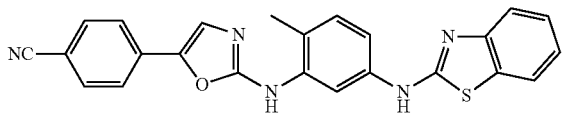 [SMILES: Cc1ccc(Nc2nc3ccccc3s2)cc1Nc1ncc(-c2ccc(C#N)cc2)o1]

m.p.=216-220° C.

004: N1-Benzooxazol-2-yl-4-methyl-N3-(5-pyridin-3-yl-oxazol-2-yl)-benzene-1,3-diamine

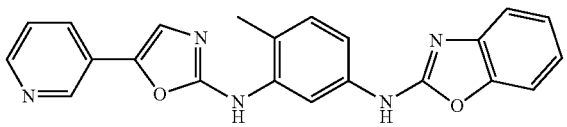 [SMILES: Cc1ccc(Nc2nc3ccccc3o2)cc1Nc1ncc(-c2cccnc2)o1]

m.p.=238° C.

005: N1-(5-Chloro-benzooxazol-2-yl)-4-methyl-N3-(5-pyridin-4-yl-oxazol-2-yl)-benzene-1,3-diamine

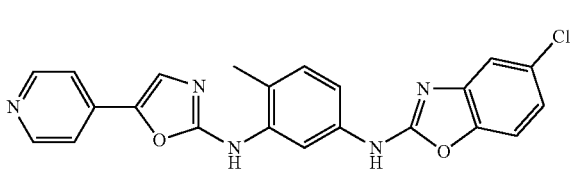 [SMILES: Cc1ccc(Nc2nc3cc(Cl)ccc3o2)cc1Nc1ncc(-c2ccncc2)o1]

m.p.=229° C.

006: N1-(6-Chloro-benzooxazol-2-yl)-4-methyl-N3-(5-pyridin-4-yl-oxazol-2-yl)-benzene-1,3-diamine

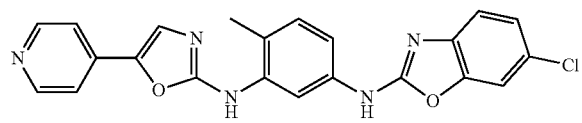 [SMILES: Cc1ccc(Nc2nc3ccc(Cl)cc3o2)cc1Nc1ncc(-c2ccncc2)o1]

m.p.>260° C.

007: N1-(5-Ethanesulfonyl-benzooxazol-2-yl)-4-methyl-N3-(5-pyridin-4-yl-oxazol-2-yl)-benzene-1,3-diamine

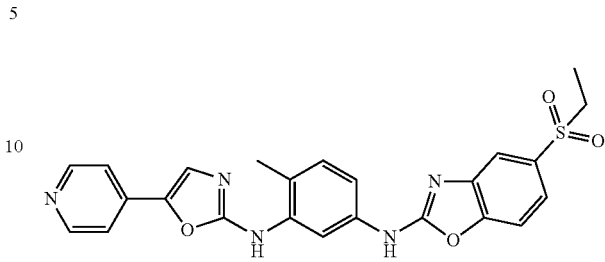

m.p.=252° C.

008: 4-Methyl-N1-(5-methyl-benzooxazol-2-yl)-N3-(5-pyridin-4-yl-oxazol-2-yl)-benzene-1,3-diamine

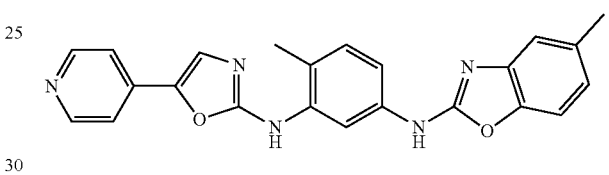

$^1$H NMR (DMSO-d$^6$, 300 MHz) δ=2.25 (s, 3H); 2.50 (s, 3H); 6.91 (d, J=8.1, 1H); 7.14 (s, 1H); 7.20 (d, J=8.4, 1H); 7.33 (d, J=8.1, 1H); 7.47-7.53 (m, 3H); 7.79 (s, 1H); 8.13 (d, J=2.1, 1H); 8.53 (s, 1H); 8.55 (s, 1H); 9.60 (s, 1H); 10.53 (s, 1H).

009: N1-(5-Fluoro-benzooxazol-2-yl)-4-methyl-N3-(5-pyridin-4-yl-oxazol-2-yl)-benzene-1,3-diamine

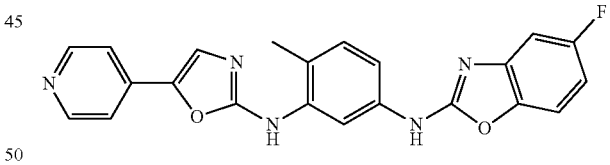

m.p.=170° C.

010: N1-(6-Fluoro-benzooxazol-2-yl)-4-methyl-N3-(5-pyridin-4-yl-oxazol-2-yl)-benzene-1,3-diamine

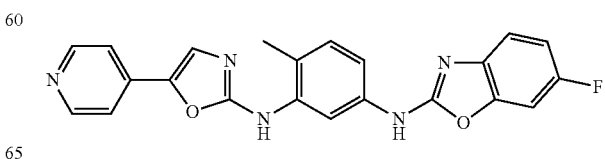

m.p.=260° C.

Among the particular compounds of formula I, the invention is directed to compounds of the following formula II:

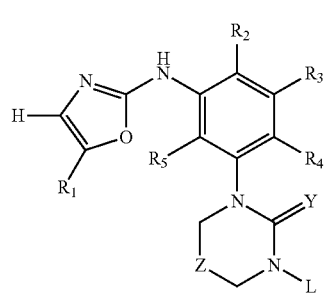

FORMULA II

Wherein Y is oxygen, sulfur, NH or N—CN, Z is oxygen, sulfur, N(R6) or (CH2)$_n$ where n is 0, 1 or 2.

L is selected from Alkyl$^1$, Aryl$^1$ or Heteroaryl$^1$ as defined above.

R1, R2, R3, R4, R5 and R6 have the meaning described above.

An example of preferred compounds of the above formula is depicted below:

011: 4-(2-{5-[3-(3-Fluoro-phenyl)-2-oxo-imidazolidin-1-yl]-2-methyl-phenylamino}-oxazol-5-yl)-benzonitrile

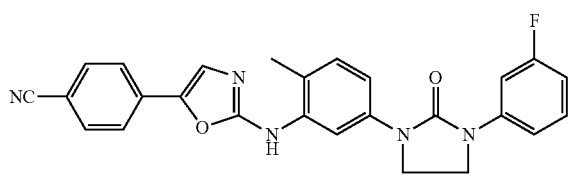 [SMILES: Cc1ccc(N2CCN(c3cccc(F)c3)C2=O)cc1Nc1ncc(-c2ccc(C#N)cc2)o1]

m.p.=221° C.

012: 4-(2-{5-[3-(3-cyano-phenyl)-2-oxo-imidazolidin-1-yl]-2-methyl-phenylamino}-oxazol-5-yl)-benzonitrile

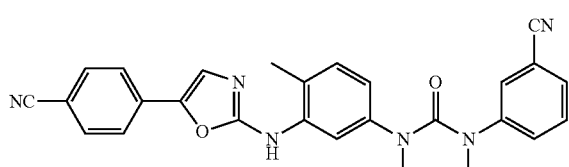

m.p.>260° C.

013: 4-(2-{5-[3-(3-Fluoro-phenyl)-2-oxo-imidazolidin-1-yl]-2-methyl-phenylamino}-oxazol-5-yl)-benzamide

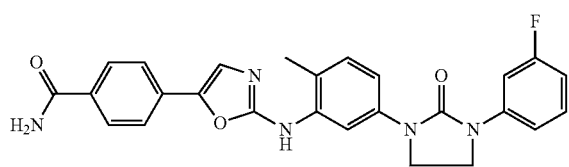 [SMILES: Cc1ccc(N2CCN(c3cccc(F)c3)C2=O)cc1Nc1ncc(-c2ccc(C(N)=O)cc2)o1]

m.p.>260° C.

014: 1-(4-Fluoro-phenyl)-3-[4-methyl-3-(5-pyridin-4-yl-oxazol-2-ylamino)-phenyl]-imidazolidin-2-one

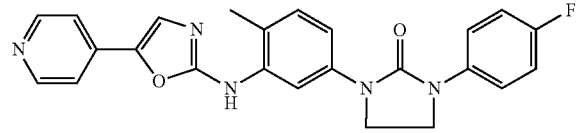 [SMILES: Cc1ccc(N2CCN(c3ccc(F)cc3)C2=O)cc1Nc1ncc(-c2ccncc2)o1]

015: 1-[4-Methyl-3-(5-pyridin-4-yl-oxazol-2-ylamino)-phenyl]-3-(3-trifluoromethyl-phenyl)-imidazolidin-2-one

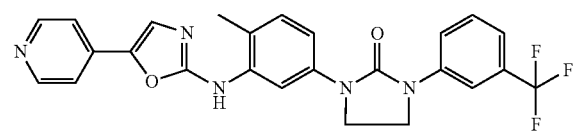 [SMILES: Cc1ccc(N2CCN(c3cccc(C(F)(F)F)c3)C2=O)cc1Nc1ncc(-c2ccncc2)o1]

m.p.=198-200° C.

016: 1-(4-Fluoro-phenyl)-3-[4-methyl-3-(5-pyridin-4-yl-oxazol-2-ylamino)-phenyl]-tetrahydro-pyrimidin-2-one

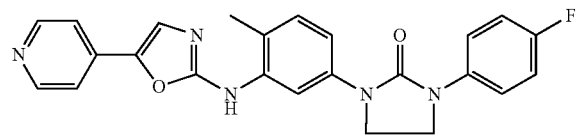 [SMILES: Cc1ccc(N2CCN(c3ccc(F)cc3)C2=O)cc1Nc1ncc(-c2ccncc2)o1]

Among the particular compounds of formula I, the invention is directed to compounds of the following formula III:

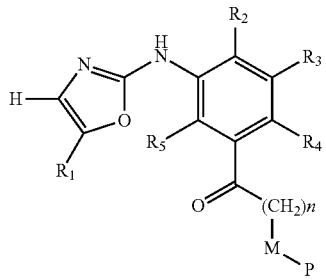

FORMULA III

With n being an integer of 0, 1 or 2.

M is oxygen, sulfur or (CH2)$_n$ where n is 0, 1 or 2.

P is selected from N(R8)(R9), Alkyl$^1$, Aryl$^1$ or Heteroaryl$^1$.

R8 and R9 each independently is hydrogen, Alkyl$^1$, Aryl$^1$ or Heteroaryl$^1$.

R8 and R9 may be taken together to form a bivalent radical of formula:

—(CH2)$_v$-X2-(CH2)$_w$-  (b)

where v and w each independently is 1 or 2 and X2 being CH2, O, S, NR10 or N[C(=O)R10] and wherein each hydrogen in said formula (b) may be substituted with halo or C$_{1-4}$alkyl.

R10 is hydrogen, C$_{1-4}$alkyl, C$_{2-6}$alkenyl, C$_{2-6}$alkynyl, C$_{3-7}$cycloalkyl, C$_{1-4}$haloalkyl, C$_{1-6}$alkoxy, C$_{1-4}$hydroxyalkyl.

R1, R2, R3, R4 and R5 have the meaning described above.

Examples

017: 1-[4-Methyl-3-(5-pyridin-4-yl-oxazol-2-ylamino)-phenyl]-3-phenyl-propan-1-one

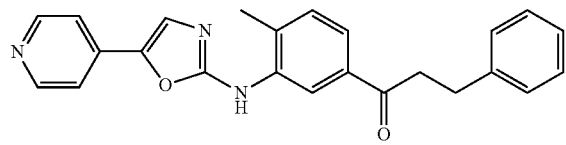 [SMILES: Cc1ccc(C(=O)CCc2ccccc2)cc1Nc1ncc(-c2ccncc2)o1]

m.p.=138° C.

018: 4-[2-(5-Acetyl-2-methyl-phenylamino)-oxazol-5-yl]-benzonitrile

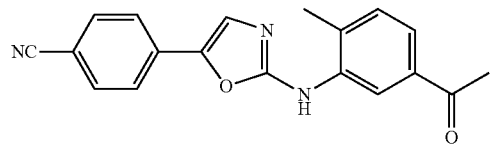 [SMILES: CC(=O)c1ccc(C)c(Nc2ncc(-c3ccc(C#N)cc3)o2)c1]

m.p.=240° C.

019: 4-(2-{5-[3-(4-Fluoro-phenyl)-propionyl]-2-methyl-phenylamino}-oxazol-5-yl)-benzonitrile

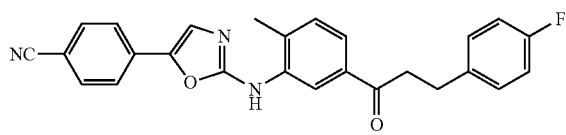 [SMILES: Cc1ccc(C(=O)CCc2ccc(F)cc2)cc1Nc1ncc(-c2ccc(C#N)cc2)o1]

m.p.=175° C.

020: 4-{2-[2-Methyl-5-(3-phenyl-propionyl)-phenylamino]-oxazol-5-yl}-benzonitrile

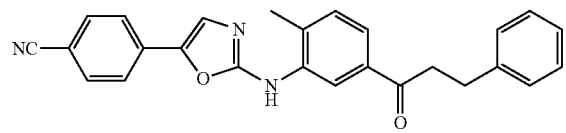 [SMILES: Cc1ccc(C(=O)CCc2ccccc2)cc1Nc1ncc(-c2ccc(C#N)cc2)o1]

m.p.=138° C.

021: 4-(2-{5-[3-(3-Fluoro-phenyl)-propionyl]-2-methyl-phenylamino}-oxazol-5-yl)-benzonitrile

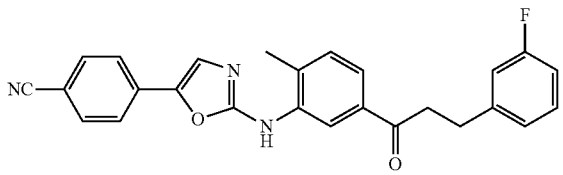 [SMILES: Cc1ccc(C(=O)CCc2cccc(F)c2)cc1Nc1ncc(-c2ccc(C#N)cc2)o1]

m.p.=157° C.

022: 4-[2-(5-Acetyl-2-methyl-phenylamino)-oxazol-5-yl]-benzamide

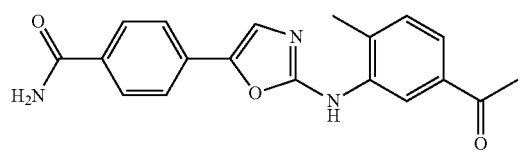 [SMILES: CC(=O)c1ccc(C)c(Nc2ncc(-c3ccc(C(N)=O)cc3)o2)c1]

m.p.>260° C.

Among the particular compounds of formula I, the invention is directed to compounds of the following formula IV:

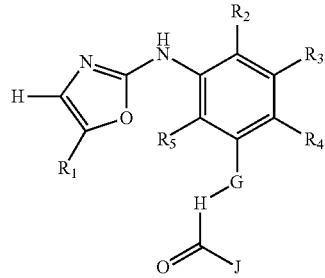

FORMULA IV

G is oxygen, sulfur, N(R11) or (CH2)$_n$ where n is 1 or 2.

H is oxygen, N(R11) or (CH2)$_n$ where n is 1 or 2.

J is selected from N(R12)(R13), Alkyl$^1$, Aryl$^1$ or Heteroaryl$^1$.

R12 and R13 each independently is hydrogen, Alkyl$^1$, Aryl$^1$ or Heteroaryl$^1$.

R12 and R13 may be taken together to form a bivalent radical of formula:

—(CH2)$_v$-X2-(CH2)$_w$-  (c)

where v and w each independently is 1 or 2 and X2 being CH2, O, S, NR14 or N[C(=O)R14] and wherein each hydrogen in said formula (c) may be substituted with halo or C$_{1-4}$alkyl.

R11 and R14 each independently is hydrogen, C$_{1-4}$alkyl, C$_{2-6}$alkenyl, C$_{2-6}$alkynyl, C$_{3-7}$cycloalkyl, C$_{1-4}$haloalkyl, C$_{1-6}$alkoxy, C$_{1-4}$hydroxyalkyl.

R1, R2, R3, R4 and R5 have the meaning described above.

Examples

023: 1-(4-Fluoro-phenyl)-2-[4-methyl-3-(5-pyridin-4-yl-oxazol-2-ylamino)-phenylamino]-ethanone

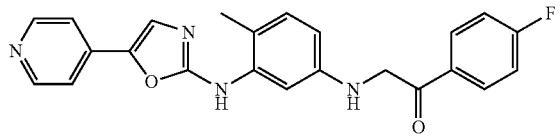 [SMILES: Cc1ccc(NCC(=O)c2ccc(F)cc2)cc1Nc1ncc(-c2ccncc2)o1]

m.p.=202° C.

024: 1-(4-Fluoro-phenyl)-2-{methyl-[4-methyl-3-(5-pyridin-4-yl-oxazol-2-ylamino)-phenyl]-amino}-ethanone

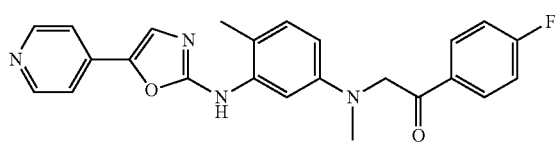 [SMILES: Cc1ccc(N(C)CC(=O)c2ccc(F)cc2)cc1Nc1ncc(-c2ccncc2)o1]

m.p.=230° C.

025: 4-({Methyl-[4-methyl-3-(5-pyridin-4-yl-oxazol-2-ylamino)-phenyl]-amino}-acetyl)-benzonitrile

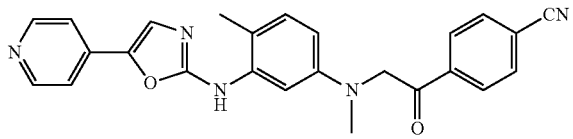 [SMILES: Cc1ccc(N(C)CC(=O)c2ccc(C#N)cc2)cc1Nc1ncc(-c2ccncc2)o1]

m.p.=218° C.

026: 2-[4-Methyl-3-(5-pyridin-4-yl-oxazol-2-ylamino)-phenylamino]-1-phenyl-ethanone

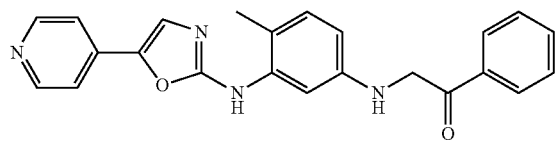 [SMILES: Cc1ccc(NCC(=O)c2ccccc2)cc1Nc1ncc(-c2ccncc2)o1]

m.p.=152° C.

027: 4-(2-{5-[2-(4-Fluoro-phenyl)-2-oxo-ethylamino]-2-methyl-phenylamino}-oxazol-5-yl)-benzonitrile

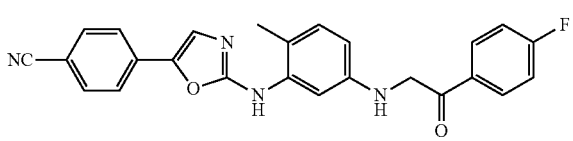 [SMILES: Cc1ccc(NCC(=O)c2ccc(F)cc2)cc1Nc1ncc(-c2ccc(C#N)cc2)o1]

m.p.=199° C.

028: 4-(2-{5-[2-(4-Cyano-phenyl)-2-oxo-ethylamino]-2-chloro-phenylamino}-oxazol-5-yl)-benzonitrile

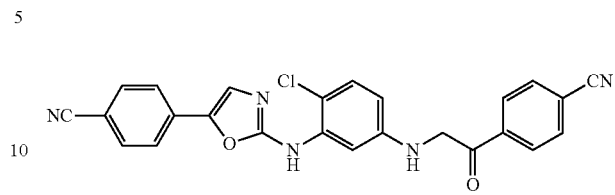

029: N-[4-Methyl-3-(5-pyridin-4-yl-oxazol-2-ylamino)-benzyl]-benzamide

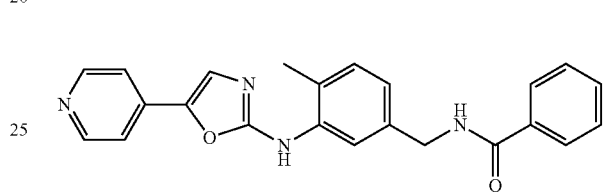

$^1$H NMR (DMSO-d$^6$, 300 MHz) δ=2.25 (s, 3H); 4.45 (d, J=5.7, 2H); 6.99 (d, J=7.2, 1H); 7.17 (d, J=7.2, 1H); 7.45-7.52 (m, 5H); 7.72 (s, 2H); 7.88 (d, J=7.2, 2H); 8.49 (d, J=5.1, 2H); 9.05 (t, J=5.7, 1H); 9.54 (s, 1H).

030: 2-{Methyl-[4-methyl-3-(5-pyridin-4-yl-oxazol-2-ylamino)-phenyl]-amino}-1-phenyl-ethanone

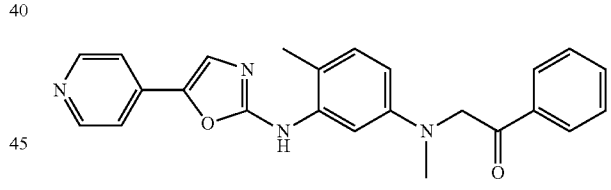

$^1$H NMR (DMSO-d$^6$, 300 MHz) δ=2.14 (s, 3H); 3.00 (s, 3H); 4.96 (s, 2H); 6.37 (d, J=9.2, 1H); 6.95 (d, J=8.4, 1H); 7.13 (s, 1H); 7.42 (d, J=5.4, 2H); 7.52-7.65 (m, 4H); 7.99 (d, J=7.2, 2H); 8.51 (d, J=5.7, 2H); 9.37 (s, 1H).

The compounds of the present invention may be prepared using the general protocol as follows:

Compounds of formula 4 can be prepared by the condensation of an azide of general formula 1 with an isocyanate of the type 2 or an isothiocyanate of the type 3.

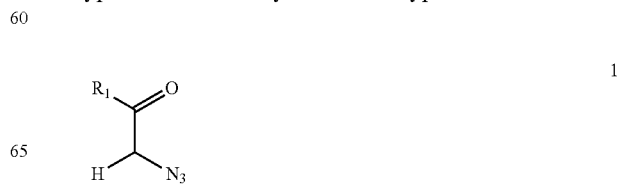

-continued

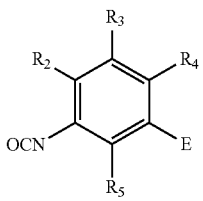
2

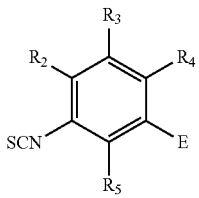
3

Group E in formula 2 and 3 corresponds to nitro, cyano, CH2OH, CO2CH3, CONH2, COCH3 or to A-B-B'-Q group. A-B-B'-Q group is as described in formula I. The reaction of 1 either with 2 or 3 in a solvent such as methylene chloride or dioxane in the presence of triphenylphosphine, leads to an oxazole-type product of formula 4.

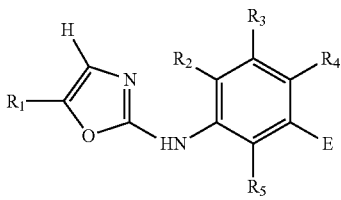
4

R1, R2, R3, R4 and R5 have the meaning described above.
The following example is intended to illustrate the present invention.

Example of Compound Synthesis

General: All chemicals used were commercial reagent grade products. Solvents were of anhydrous commercial grade and were used without further purification. Dioxane is freshly distilled under a stream of argon before use. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were realized on a 300 MHz Bruker spectrometer.

Preparation of 4-Azido acetyl-benzonitrile

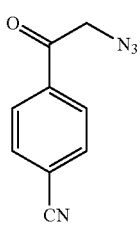 [SMILES: N#Cc1ccc(C(=O)CN=[N+]=[N-])cc1]

To a solution of the commercially available 4-bromoacetyl-benzonitrile (5 g, 22.32 mmol) in 150 mL of methanol was added sodium azide (1.74 g, 26.78 mmol) and the contents stirred at room temperature for 2 h. After removal of the solvent, the residue was treated with water (50 mL) and extracted with dichloromethane (3×50 mL). The combined organic layers were dried over MgSO$_4$ and concentrated to give a yellow solid (3.90 g, 94%). This compound was used for the next step without any further purification.

Preparation of 4-[2-(2-Methyl-5-nitro-phenylamino)-oxazol-5-yl]-benzonitrile

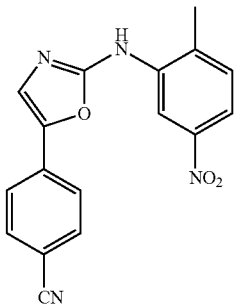

To a solution of 4-Azidoacetyl-benzonitrile (1.5 g, 8.06 mmol) in dioxane 25 mL was added 2-methyl-5-nitrophenyl isocyanate (1.43 mg, 8.06 mmol) (commercially available), and triphenylphosphine (2.11 g, 8.06 mmol). The reaction mixture was placed in an oil bath preheated to 100° C. and stirred for 30 min. After evaporation of the solvent under reduced pressure, the solid residue was recrystallized from ethanol to give the title compound as yellow micro crystals (1.16 g, 45%).
m.p.>260° C.

Preparation of 4-[2-(5-Amino-2-methyl-phenylamino)-oxazol-5-yl]-benzonitrile

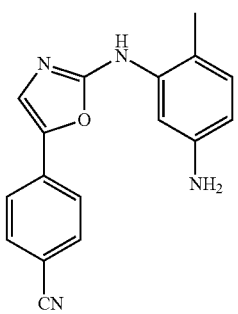 [SMILES: Cc1ccc(N)cc1Nc1ncc(-c2ccc(C#N)cc2)o1]

To a solution of 4-[2-(2-Methyl-5-nitro-phenylamino)-oxazol-5-yl]-benzonitrile (500 mg, 1.56 mmol) in ethanol (15 mL) was added tin(II) chloride dihydrate (677 mg, 3 mmol). The reaction mixture was heated under reflux for 4 h. The mixture was then concentrated, saturated aqueous NaHCO$_3$ was added and the resultant suspension was extracted with ethyl acetate (3×15 mL). The combined organic layers were washed with brine (30 mL), dried over anhydrous MgSO$_4$ and concentrated. The residue was alumina column chromatographed (dichloromethane/ethanol: 99/1). 4-[2-(5-Amino-2-methyl-phenylamino)-oxazol-5-yl]-benzonitrile was obtained as pale yellow powder (172 mg, 38%).
m.p.=236° C.

$^1$H NMR (DMSO-d$^6$) δ=2.14 (s, 3H); 4.91 (br s, 2H); 6.25 (dd, J=7.8-1.9, 1H); 6.82 (d, J=8.0, 1H); 7.01 (d, J=2.4, 1H); 7.68 (m, 3H); 7.84 (d, J=8.5, 2H); 9.22 (s, 1H).

Preparation of 4-(2-{5-[2-(4-Fluoro-phenyl)-2-oxo-ethylamino]-2-methyl-phenyl amino}-oxazol-5-yl)-benzonitrile

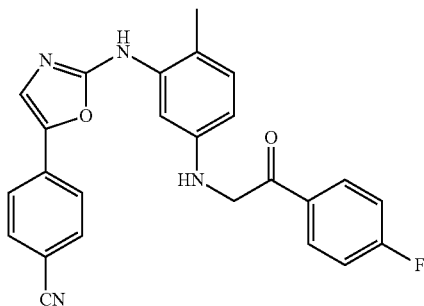 [SMILES: Cc1ccc(NCC(=O)c2ccc(F)cc2)cc1Nc1ncc(-c2ccc(C#N)cc2)o1]

To a solution of 4-[2-(5-Amino-2-methyl-phenylamino)-oxazol-5-yl]-benzonitrile (60 mg, 0.207 mmol) in dimethylacetamide (3 mL) was added 4-fluorophenacyl bromide (45 mg, 0.207 mmol), NaHCO$_3$ (18 mg, 0.207 mmol). The mixture was stirred at room temperature for 2 h. After removal of the solvent, the residue was treated with saturated aqueous NaHCO$_3$ (10 mL) and extracted with ethyl acetate (3×10 mL). The combined organic layers were washed with brine (20 mL), dried over MgSO$_4$ and concentrated. 4-(2-{5-[2-(4-Fluoro-phenyl)-2-oxo-ethylamino]-2-methyl-phenyl amino}-oxazol-5-yl)-benzonitrile was obtained after silica gel column chromatography (dichloromethane/ethanol: 9812) (38 mg, 43%) as beige solid.

m.p.=199° C.

$^1$H NMR (DMSO-d$^6$) δ=2.12 (s, 3H); 4.62 (d, J=4.8, 2H); 5.81 (t, J=4.8, 1H); 6.37 (d, J=6.0, 1H); 6.91 (d, J=8.1, 1H); 7.08 (s, 1H); 7.37 (m, 2H); 7.67 (m, 3H); 7.83 (d, J=8.4, 2H); 8.14 (m, 2H); 9.30 (s, 1H).

Preparation of 4-[2-(5-Acetyl-2-methyl-phenylamino)-oxazol-5-yl]-benzonitrile

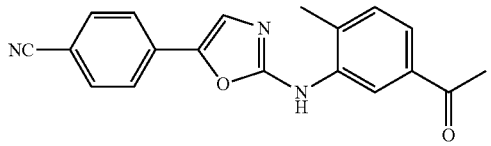 [SMILES: CC(=O)c1ccc(C)c(Nc2ncc(-c3ccc(C#N)cc3)o2)c1]

In a similar manner as described for the preparation of 4-[2-(2-Methyl-5-nitro-phenylamino)-oxazol-5-yl]-benzonitrile, from 4-Azidoacetyl-benzonitrile (2.70 g, 14.5 mmol) and 1-(3-Isothiocyanato-4-methyl-phenyl)-ethanone (2.22 g, 11.6 mmol) was obtained the title compound (1.43, 31%), as a yellow solid.

$^1$H NMR (DMSO-d$^6$) δ=2.41 (s, 3H); 2.59 (s, 3H); 7.41 (d, J=7.8, 1H); 7.67 (dd, J=7.8-1.6, 1H); 7.75 (s, 1H); 7.79 (d, J=8.4, 2H); 7.72 (d, J=8.4, 2H); 8.51 (d, J=1.6, 1H); 9.73 (s, 1H).

Preparation of 4-{2-[2-Methyl-5-(3-phenyl-propionyl)-phenylamino]-oxazol-5-yl}-benzonitrile

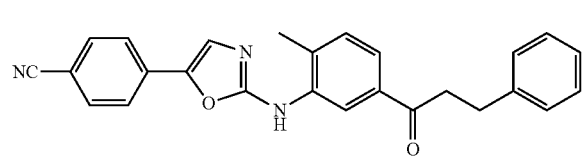 [SMILES: Cc1ccc(C(=O)CCc2ccccc2)cc1Nc1ncc(-c2ccc(C#N)cc2)o1]

To a stirred solution of 4-[2-(5-Acetyl-2-methyl-phenylamino)-oxazol-5-yl]-benzonitrile (100 mg, 0.315 mmol) and benzaldehyde (0.035 mL, 0.35 mmol) in ethanol, was added dropwise at 0° C., 1 mL of aqueous NaOH 30%. After the mixture was stirred at room temperature for 16 h and poured into ice water (ca. 10 mL). The precipitate was filtered, washed diethyl ether and dried under vacuum.

The yellow solid obtained was dissolved in ethanol (2 mL) and THF (2 mL), treated with palladium on carbon (10%, 20 mg) and hydrogenated. The catalyst was removed by filtration through a pad of celite. The filtrate was evaporated under reduce pressure to give the title compound (77 mg, 60%) as yellow powder.

$^1$H NMR (DMSO-d$^6$) δ=2.41 (s, 3H); 2.98 (t, J=7.7, 2H); 3.36 (t, J=7.7, 2H); 7.23 (m, 1H); 7.32 (m, 4H); 7.40 (d, J=7.8, 1H); 7.69 (dd, J=7.8-1.6, 1H); 7.72 (s, 1H); 7.89 (d, J=8.4, 2H); 7.94 (d, J=8.4, 2H); 8.52 (d, J=1.6, 1H); 9.73 (s, 1H).

Preparation of 4-Bromoacetylpyridine, HBr salt

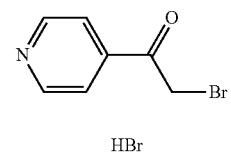

Bromine (24 g, 150 mmol) in 4 mL of 45% HBr was added drop wise under vigorous stirring to a solution at 70° C. of 4-acetyl-pyridine (18 g, 148 mmol) in acetic acid containing 45% of HBr (165 mL). The vigorously stirred mixture was kept at 70° C. for 3 h. The mixture was cooled and the precipitate collected by filtration and washed with petroleum ether (40-65° C.)/methanol (1/1, 100 mL) to give 35.8 g of a white crystals of (85%).

Preparation of 2-Methyl-5-nitro-phenyl)-(5-pyridin-4-yl-oxazol-2-yl)-amine

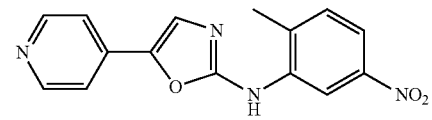

To a solution of 4-bromoacetylpyridine hydrobromide (5 g, 17.8 mmol) in 80 mL of water was added sodium azide (1.16 g, 17.8 mmol) and the contents stirred at room temperature for 30 min. The reaction mixture was cooled to 0° C., treated slowly with saturated aqueous NaHCO₃ until pH=6-7, extracted with dichloromethane (3×30 mL) and the combined organic phases were dried over MgSO₄, concentrated at room temperature under reduced pressure to a final volume of 25 mL, and diluted with dioxane (30 mL). The resulting solution was concentrated to remove the remaining (lower boiling) dichloromethane. To the final volume (25 mL) was added at 0° C., 2-methyl-5-nitrophenyl isocyanate (1.58 g, 8.9 mmol) (commercially available) and portion wise triphenylphosphine (2.62 g, 8.9 mmol). The reaction mixture was then stirred for 1 h at room temperature and heated for an additional 2 h at 100° C. After evaporation of the solvent under reduced pressure the residue was crystallized in dichloromethane/ethanol (10 mL/5 mL), to give the title compound as yellow crystals (0.9 g, 34%).

m p>220° C.

Preparation of (2-Methyl-5-amino-phenyl)-(5-pyridin-4-yl-oxazol-2-yl)-amine

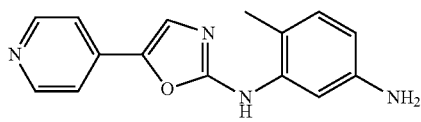 [SMILES: Cc1ccc([N+](=O)[O-])cc1Nc1ncc(-c2ccncc2)o1]

A solution of (2-methyl-5-nitro-phenyl)-(5-pyridin-4-yl-oxazol-2-yl)-amine (1 g, 3.39 mmol) in ethanol (50 mL) was treated with 10% Pd/C (120 mg) and hydrazine hydrate (3.50 mL, 112.5 mmol) was added drop wise over 10 min. The reaction mixture was stirred at room temperature for 30 min and then refluxed for 2 h. The hot solution was filtered through a short pad of Celite, and the catalyst was washed with hot ethanol. The filtrates were concentrated under reduced vacuum to give the crude product. This was silica gel column chromatographed (dichloromethane/ethanol: 97/3). 720 mg (80%) of (2-methyl-5-amino-phenyl)-(5-pyridin-4-yl-oxazol-2-yl)-amine was obtained as pale yellow powder.

m p 158° C.

¹H NMR (DMSO-d⁶) δ=2.14 (s, 3H); 4.96 (bs, 2H); 6.30 (dd, J=8.1-2.1, 1H); 6.87 (d, J=8.1, 1H); 7.04 (d, J=2.1, 1H); 7.50 (d, J=6.0, 2H); 8.58 (d, J=6.0, 2H); 7.76 (s, 1H); 9.28 (s, 1H).

Preparation of (5-Isothiocyanato-2-methyl-phenyl)-(5-pyridin-4-yl-oxazol-2-yl)-amine

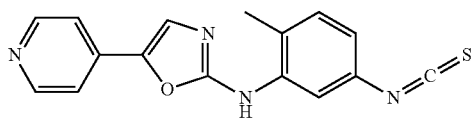 [SMILES: Cc1ccc(N=C=S)cc1Nc1ncc(-c2ccncc2)o1]

To a solution of (2-Methyl-5-amino-phenyl)-(5-pyridin-4-yl-oxazol-2-yl)-amine (500 mg, 1.88 mmol) in dichloromethane (70 mL) was added 1,1'-Thiocarbonyldi-2(1H)-pyridine (525 mg, 2.26 mmol). The mixture was stirred at room temperature overnight. After evaporation of the solvent under reduced pressure, the residue was silica gel column chromatographed (ethyl acetate/heptane 50/50) to give 528 mg (91%) of the title compound as a beige solid.

¹H NMR (DMSO-d⁶) δ=2.36 (s, 3H); 7.10 (dd, J=8.1-2.1, 1H); 7.32 (d, J=8.1, 1H); 7.56 (d, J=6.0, 2H); 7.86 (s, 1H); 8.08 (d, J=2.1, 1H); 8.62 (d, J=6.0, 2H); 9.80 (s, 1H).

Preparation of N1-(5-Chloro-benzooxazol-2-yl)-4-methyl-N3-(5-pyridin-4-yl-oxazol-2-yl)-benzene-1,3-diamine

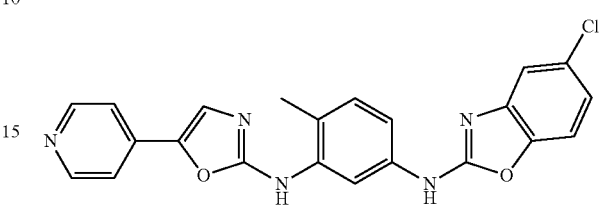

To a solution of (5-Isothiocyanato-2-methyl-phenyl)-(5-pyridin-4-yl-oxazol-2-yl)-e (120 mg, 0.39 mmol) in DMF (8 mL), was added 2-Amino-4-chloro-phenol (61 mg, 0.43 mmol). The mixture was stirred at room temperature overnight and yellow Mercury (II) oxide (72 mg, 0.39 mmol) was added. The mixture was stirred at room temperature 1 h the precipitate was filtered through a short pad of Celite. The filtrate was concentrated under reduced vacuum to give the crude product. This was silica gel column chromatographed (dichloromethane/ethanol: 95/5) to give 112 mg (69%) of the title compound as a yellow solid.

¹H NMR (DMSO-d⁶) δ=2.26 (s, 3H); 7.14 (dd, J=8.7-2.1, 1H); 7.22 (d, J=8.7, 1H); 7.40 (d, J=2.1, 1H); 7.47-7.53 (m, 4H); 7.79 (s, 1H); 8.12 (d, J=2.1, 1H); 8.53 (s, 1H); 8.55 (s, 1H); 9.61 (s, 1H); 10.77 (s, 1H).

Preparation of 4-(2-{5-[3-(3-Fluoro-phenyl)-2-oxo-imidazolidin-1-yl]-2-methyl-phenylamino}-oxazol-5-yl)-benzonitrile

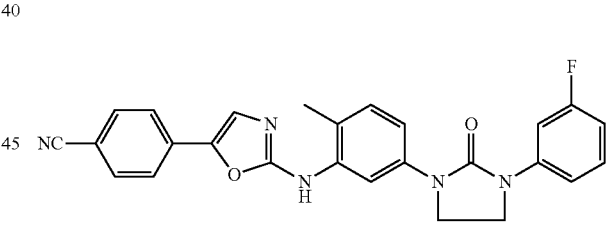

To a solution of 4-[2-(5-Amino-2-methyl-phenylamino)-oxazol-5-yl]-benzonitrile (558 mg, 2 mmol) and chloroacetaldehyde (50 wt. % in water, 628 mg, 4 mmol) in acetonitril (60 mL), was added at RT NaBH₃CN (253 mg, 4 mmol) and dropwise acetic acid (0.4 mL). The mixture was stirred at room temperature 1 h. Ethyl acetate (50 mL) and saturated aqueous NaHCO₃ (50 mL) were added. The organic layer was washed with brine (20 mL), dried over MgSO₄ and concentrated to give a yellow solid. This was dissolved in toluene (40 mL) and treated with 1-Fluoro-3-isocyanato-benzene (274 mg, 2 mmol) at reflux for 2 h. After evaporation of solvent under reduced vacuum, the crude product was dissolved in isopropanol (60 mL) and treated with potassium tert-butoxide (1.8 g, 16 mmol) at RT for 5 h. Water (20 mL) was added, the organic layer was separated dried over MgSO₄ and concentrated. The crude product was silica gel column chromatographed (dichloromethane/ethanol: 95/5) to give 408 mg (45%) of the title compound as a beige solid.

$^1$H NMR (DMSO-d$^6$) δ=2.26 (s, 3H); 3.98 (s, 4H); 6.90 (t, J=9.0, 1H); 7.20 (bs, 2H); 7.33-7.42 (m, 2H); 7.65-7.85 (m, 6H); 8.19 (s, 1H); 9.82 (s, 1H).

Preparation of 4-(2-{5-[3-(3-Fluoro-phenyl)-2-oxo-imidazolidin-1-yl]-2-methyl-phenylamino}-oxazol-5-yl)-benzonitrile

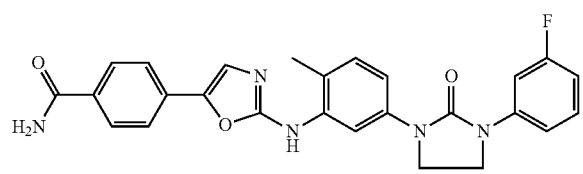 [SMILES: Cc1ccc(N2CCN(c3cccc(F)c3)C2=O)cc1Nc1ncc(-c2ccc(C(N)=O)cc2)o1]

Compound 4-(2-{5-[3-(3-Fluoro-phenyl)-2-oxo-imidazolidin-1-yl]-2-methyl-phenyl amino}-oxazol-5-yl)-benzonitrile (30 mg, 0.066 mmol), was treated in EtOH (2 mL) with 3N NaOH (1 mL). The resulting mixture was stirred at reflux for 3 h. After cooling to RT, 1N HCl was added until pH=6-7 and the precipitate filtered to give the title compound as a yellow solid (9 mg, 29%).

ES/MS: m/z=471 [M-H]$^-$.

In a second embodiment, the invention relates to a pharmaceutical composition comprising a compound as depicted above.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension, aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit and/or a bcr-abl inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V.60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biology of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
- liquid gas systems (a liquefied gas is used as propellant gas (e.g. low-boiling FCHC or propane, butane) in a pressure container,
- suspension aerosol (the active substance particles are suspended in solid form in the liquid propellant phase),
- pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellant gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to unregulated c-kit transduction comprising administering an effective amount of a compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount a compound depicted above to a mammal in need of such treatment.

The above described compounds are useful for manufacturing a medicament for the treatment of diseases related to unregulated c-kit transduction, including, but not limited to:
- neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.
- tumor angiogenesis.
- metabolic diseases such as diabetes mellitus and its chronic complications; obesity; diabete type II; hyperlipidemias and dyslipidemias; atherosclerosis; hypertension; and cardiovascular disease.
- allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.
- interstitial cystitis.
- bone loss (osteoporosis).

inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

Other autoimmune diseases embraced by the invention active chronic hepatitis and chronic fatigue syndrome.

subepidermal blistering disorders such as pemphigus.

Vasculitis.

HIV infection.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

substance use disorders as referred herein include but are not limited to drug addiction, drug abuse, drug habituation, drug dependence, withdrawal syndrome and overdose.

Cerebral ischemia

Fibrosis

Duchenne muscular dystrophy

Regarding mastocytosis, the invention contemplates the use of the compounds as defined above for treating the different categories which can be classified as follows:

The category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

The category II includes mastocytosis with an associated hematological disorder, such as a myeloproliferative or myelodysplastic syndrome, or acute leukemia. These malignant mastocytosis does not usually involve the skin. The progression of the disease depends generally on the type of associated hematological disorder that conditions the prognosis.

The category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, the category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobactor freudii* and *Salmonella typhimurium*. In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

Example: In Vitro TK Inhibition Assays

Procedures
C-Kit WT and Mutated C-Kit (JM and Kinase Domain 816) Assay
Proliferation Assays Cells were washed two times in PBS before plating at $5 \times 10^4$ cells per well of 96-well plates in triplicate and stimulated either with hematopoietic growth factors (HGF) or without. After 2 days of culture, 37 Bq (1.78 Tbq/mmol) of [$^3$H] thymidine (Amersham Life Science, UK) was added for 6 hours. Cells were harvested and filtered through glass fiber filters and [$^3$H] thymidine incorporation was measured in a scintillation counter.

For proliferation assay, all drugs were prepared as 20 mM stock solutions in DMSO and conserved at −80° C. Fresh dilutions in PBS were made before each experiment. DMSO dissolved drugs were added at the beginning of the culture. Control cultures were done with corresponding DMSO dilutions. Results are represented in percentage by taking the proliferation without inhibitor as 100%.

Cells
Ba/F3 murine kit and human kit, Ba/F3 mkitΔ27 (juxtamembrane deletion), and hkitD816V are derived from the murine IL-3 dependent Ba/F3 proB lymphoid cells. The FMA3 and P815 cell lines are mastocytoma cells expressing endogenous mutated forms of Kit, i.e., frame deletion in the murine juxtamembrane coding region of the receptor-codons 573 to 579. The human leukaemic MC line HMC-1 expresses a double point mutation (i.e. mutations JM-V560G and the kinase domain mutation kitD816V), whereas the HMC1 subclone α155 expresses only the mutation JM-V560G.

Immunoprecipitation Assays and Western Blotting Analysis

For each assay, $5.10^6$ Ba/F3 cells and Ba/F3-derived cells with various c-kit mutations were lysed and immunoprecipitated as described (Beslu et al., 1996), excepted that cells were stimulated with 250 ng/ml of rmKL. Cell lysates were immunoprecipitated with rabbit immunsera directed against the KIT cytoplasmic domain either with an anti murine KIT (Rottapel et al., 1991) or an anti human KIT (Santa Cruz). Western blot was hybridized either with the 4G10 anti-phosphotyrosine antibody (UBI) or with the appropriate rabbit immunsera anti KIT or with different antibodies (described in antibodies paragraph). The membrane was then incubated either with HRP-conjugated goat anti mouse IgG antibody or with HRP-conjugated goat anti rabbit IgG antibody (Immunotech), Proteins of interest were then visualized by incubation with ECL reagent (Amersham).

Experimental Results

The experimental results for various compounds according to the invention using above-described protocols are set forth at Table 1:

TABLE 1 in vitro inhibitions of various compounds against
c-Kit WT, c-Kit JMΔ27 and c-Kit D816V.

| Target | IC50 (μM) | Compounds |
|---|---|---|
| c-Kit WT | IC50 < 1 μM | 001; 002; 004; 011; 017; 021; 028; 030 |
| c-Kit JMΔ27 | IC50 < 1 μM | 001; 017; 027; 028; 029; 030 |
| c-Kit D816V | IC50 ≤ 1 μM | 001; 002; 011; 017; 021; 030 |

We claim:
1. A compound of formula II:

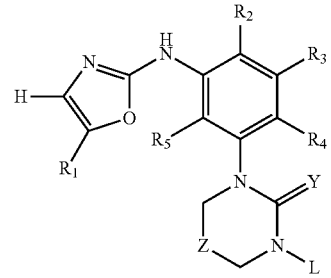

FORMULA II wherein:
Y is oxygen, sulfur, NH or N—CN,
Z is (CH2)$_n$ where n is 0,
L is selected from:
an Alkyl$^1$ group defined as a linear, branched or cycloalkyl group containing from 1 to 10 carbon atoms and optionally substituted with one or more heteroatoms selected from F, Cl, Br, I, oxygen, and nitrogen (the latter optionally in the form of a pendant basic nitrogen functionality); trifluoromethyl, carboxyl, cyano, nitro, formyl; CO—R, COO—R, CONH—R, SO2-R, and SO2NH—R wherein R is a linear or branched alkyl group containing 1 to 10 carbon atoms and optionally substituted with at least one heteroatom selected from F, Cl, Br, I, oxygen, and nitrogen, the latter optionally in the form of a pendant basic nitrogen functionality; a cycloalkyl or aryl$^1$ or heteroaryl¹ group optionally substituted by a pendant basic nitrogen functionality, an Aryl¹ group defined as a phenyl or a substituted variant thereof bearing one or more substituents selected from:
I, F, Cl or Br;
an alkyl¹ group;
a cycloalkyl, aryl or heteroaryl group optionally substituted by a pendant basic nitrogen functionality;
trifluoromethyl, O-alkyl¹, carboxyl, cyano, nitro, formyl, hydroxy, NH-alkyl¹, N(alkyl¹)(alkyl¹), and amino;
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^s$, aryl or heteroaryl, and a Heteroaryl¹ group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, benzoxazole, benzothiazole, quinolinyl group, which may additionally bear one or more substituents selected from:
F, Cl, Br or I;
an alkyl¹ group;
a cycloalkyl, aryl or heteroaryl group optionally substituted by a pendant basic nitrogen functionality,
trifluoromethyl, O-alkyl¹, carboxyl, cyano, nitro, formyl, hydroxy, NH-alkyl¹, N(alkyl¹)(alkyl¹), and amino;
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl¹;

R1 is selected from
i) an aryl¹ group, and
ii) a pyridyl group, which may additionally bear one or more substituents selected from
F, Cl, Br or I;
an alkyl¹ group;
a cycloalkyl, aryl or heteroaryl group optionally substituted by a pendant basic nitrogen functionality,
trifluoromethyl, O-alkyl¹, carboxyl, cyano, nitro, formyl, hydroxy, NH-alkyl¹, N(alkyl¹)(alkyl¹), and amino;
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl¹:

R2 is selected from hydrogen, F, Cl, Br, I, a linear or branched alkyl group containing from 1 to 10 carbon atoms and optionally substituted with one or more heteroatoms selected from F, Cl, Br, I, oxygen, and nitrogen, the latter optionally in the form of a pendant basic nitrogen functionality; trifluoromethyl, amino, $C_{1-6}$alkylamino, di($C_{1-6}$alkyl) amino, carboxyl, cyano, nitro, formyl, hydroxy, and CO—R or COO—R or CONH—R or SO2-R or SO2NH—R wherein R is a linear or branched alkyl group containing from 1 to 10 carbon atoms and optionally substituted with at least one heteroatom selected from F, Cl, Br, I, oxygen, and nitrogen, the latter optionally in the form of a pendant basic nitrogen functionality; and R3, R4 and R5 each independently are selected from hydrogen, F, Cl, Br, I, a linear or branched alkyl group containing from 1 to 10 carbon atoms and optionally substituted with one or more heteroatoms selected from F, Cl, Br, I, oxygen, and nitrogen, the latter optionally in the form of a pendant basic nitrogen functionality; trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONH—R, SO2-R, and SO2NH—R wherein R is a linear or branched alkyl group containing from 1 to 10 carbon atoms and optionally substituted with at least one heteroatom selected from F, Cl, Br, I, oxygen, and nitrogen, the latter optionally in the form of a pendant basic nitrogen functionality;

the pendant basic nitrogen functionality representing one of the following groups (a) to (m), the wavy line corresponding to the point of attachment to the core structure of formula (I):

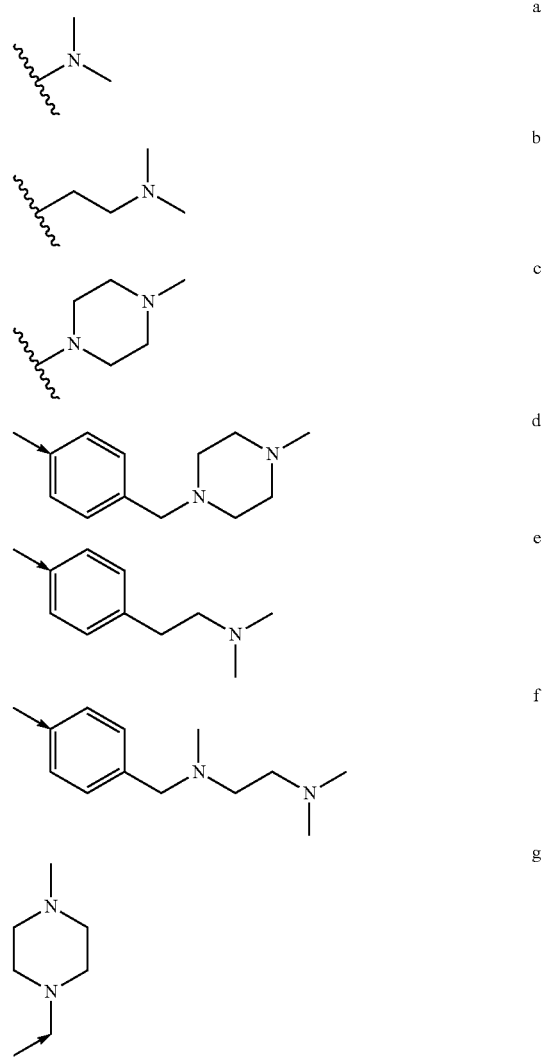

-continued

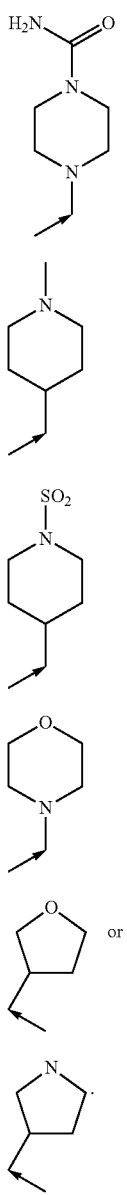

h i j k l m

2. The compound as claimed in claim 1 selected from:
4-(2-{5-[3-(3-Fluoro-phenyl)-2-oxo-imidazolidin-1-yl]-2-methyl-phenylamino}-oxazol-5-yl)-benzonitrile,
4-(2-{5-[3-(3-Cyano-phenyl)-2-oxo-imidazolidin-1-yl]-2-methyl-phenylamino}-oxazol-5-yl)-benzonitrile,
4-(2-{5-[3-(3-Fluoro-phenyl)-2-oxo-imidazolidin-1-yl]-2-methyl-phenylamino}-oxazol-5-yl)-benzamide,
1-(4-Fluoro-phenyl)-3-[4-methyl-3-(5-pyridin-4-yl-oxazol-2-ylamino)-phenyl]-imidazolidin-2-one, and
1-[4-Methyl-3-(5-pyridin-4-yl-oxazol-2-ylamino)-phenyl]-3-(3-trifluoromethyl-phenyl)-imidazolidin-2-one.

3. The compound according to claim 1, wherein R1 is pyridyl or benzonitrile which may additionally bear one or more substituents selected from
hydrogen;
F, Cl, Br or I;
alkyl$^1$ group;
aryl$^1$ group;
trifluoromethyl, O-alkyl$^1$, carboxyl, cyano, nitro, formyl, hydroxy, NH-alkyl$^1$, N(alkyl$^1$)(alkyl$^1$), and amino; and
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^1$, or aryl$^1$ group.

4. A pharmaceutical composition comprising a compound according to claim 1 and pharmaceutically acceptable carriers.

5. The pharmaceutical composition according to claim 4 comprising a pharmaceutically acceptable carrier suitable for oral or topical administration.

6. The pharmaceutical composition according to claim 4 formulated as tablets, pills, dragees, capsules, liquids, gels, syrups, slurries, and suspensions.

7. A cosmetic composition for topical administration comprising a compound according to claim 1.

8. A pharmaceutical composition comprising a compound according to claim 2, and a pharmaceutically acceptable carrier.

9. A method of treating a neoplastic disease comprising administering to a subject in need thereof an effective amount of the compound according to claim 1, wherein said neoplastic disease is mastocytosis or human gastrointestinal stromal tumor ("GIST").

10. A method of treating asthma comprising administering to a subject in need thereof an effective amount of the compound according to claim 1.

11. A method of treating rheumatoid arthritis comprising administering to a subject in need thereof an effective amount of the compound according to claim 1.

12. A method of treating multiple sclerosis comprising administering to a subject in need thereof an effective amount of the compound according to claim 1.

13. A method of treating a mastocytosis, a human gastrointestinal stromal tumor ("GIST"), asthma, rheumatoid arthritis, or multiple sclerosis, comprising administering to a subject in need thereof an effective amount of the compound according to claim 2.

* * * * *